United States Patent
Matsushima et al.

(10) Patent No.: US 7,487,646 B2
(45) Date of Patent: Feb. 10, 2009

(54) SLEEPING CAPSULE

(75) Inventors: Junji Matsushima, Sakai (JP); Tetsuya Matsuura, Sakai (JP)

(73) Assignee: Daikin Industries, Ltd., Osaka (JP)

( * ) Notice: Subject to any disclaimer, the term of this patent is extended or adjusted under 35 U.S.C. 154(b) by 426 days.

(21) Appl. No.: 10/503,500

(22) PCT Filed: Feb. 5, 2003

(86) PCT No.: PCT/JP03/01200

§ 371 (c)(1),
(2), (4) Date: May 10, 2005

(87) PCT Pub. No.: WO03/067161

PCT Pub. Date: Aug. 14, 2003

(65) Prior Publication Data

US 2005/0199736 A1    Sep. 15, 2005

(30) Foreign Application Priority Data

Feb. 8, 2002    (JP) .............................. 2002-31861

(51) Int. Cl.
*A47C 27/00* (2006.01)
*F25D 23/12* (2006.01)
*F24F 7/06* (2006.01)

(52) U.S. Cl. .............................. 62/186; 62/261; 5/423; 236/49.3; 454/251

(58) Field of Classification Search ............... 62/261, 62/186; 5/421, 423; 236/49.3; 454/239, 454/251

See application file for complete search history.

(56) References Cited

U.S. PATENT DOCUMENTS

| | | | | |
|---|---|---|---|---|
| 2,463,090 A | * | 3/1949 | Dixon et al. ................. | 62/261 |
| 2,898,837 A | | 8/1959 | Scarselli | |
| 3,724,172 A | * | 4/1973 | Wood .......................... | 95/287 |
| 4,602,486 A | * | 7/1986 | Weinstein .................... | 62/261 |
| 5,645,578 A | | 7/1997 | Daffer et al. | |

(Continued)

FOREIGN PATENT DOCUMENTS

FR    2 705 033 A1    11/1994

(Continued)

*Primary Examiner*—Marc E Norman
(74) *Attorney, Agent, or Firm*—Birch, Stewart, Kolasch & Birch, LLP

(57) ABSTRACT

A head-side inflow/outflow unit (60) and a foot-side inflow/outflow unit (70), which have a respective outlet opening (61, 71) for providing a supply of conditioned air to a sleeping compartment (11) within a capsule main body (20) and a respective inlet opening (62, 72), associated with the outlet opening (61, 71), for drawing in internal air of the sleeping compartment (11), are provided. The air-conditioning capacity of conditioned air supplied through each of the outlet openings (61, 71) is controlled such that the temperature of conditioned air supplied through the outlet opening (61) of the head-side inflow/outflow unit (60) falls below the temperature of conditioned air supplied through the outlet opening (71) of the foot-side inflow/outflow unit (70). In the head-side inflow/outflow unit (60), the inlet opening (62) is situated below the outlet opening (61), while on the other hand in the foot-side inflow/outflow unit (70) the inlet opening (72) is situated above the outlet opening (71), thereby producing flow of an air current causing a short-circuit between the outlet opening (61, 71) and the inlet opening (62, 72).

8 Claims, 17 Drawing Sheets

U.S. PATENT DOCUMENTS

2004/0242148 A1 * 12/2004 Schmid et al. .............. 454/329

FOREIGN PATENT DOCUMENTS

| JP | 4-100545 U | 8/1992 |
| JP | 4-295371 A | 10/1992 |
| JP | 08-169229 A | 7/1996 |
| JP | 09-010075 A | 1/1997 |

* cited by examiner

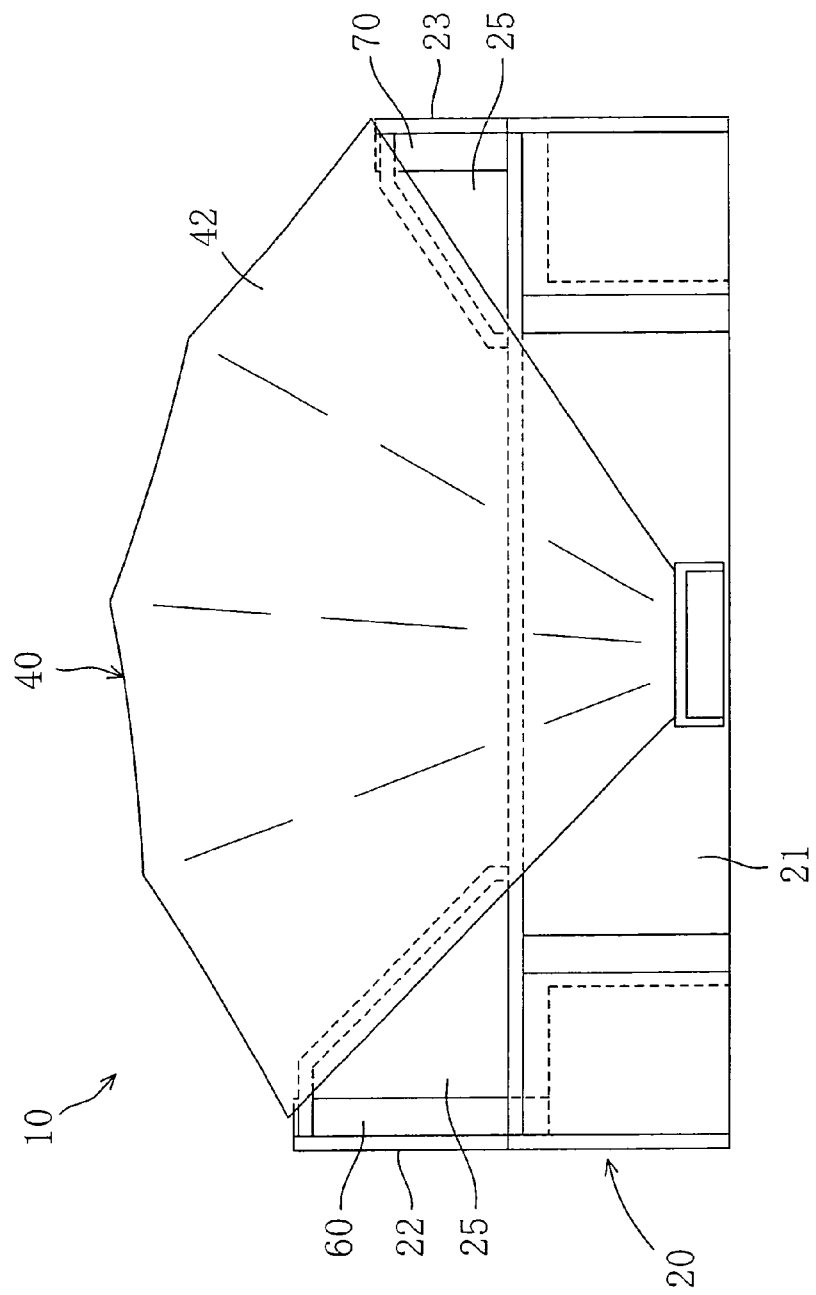

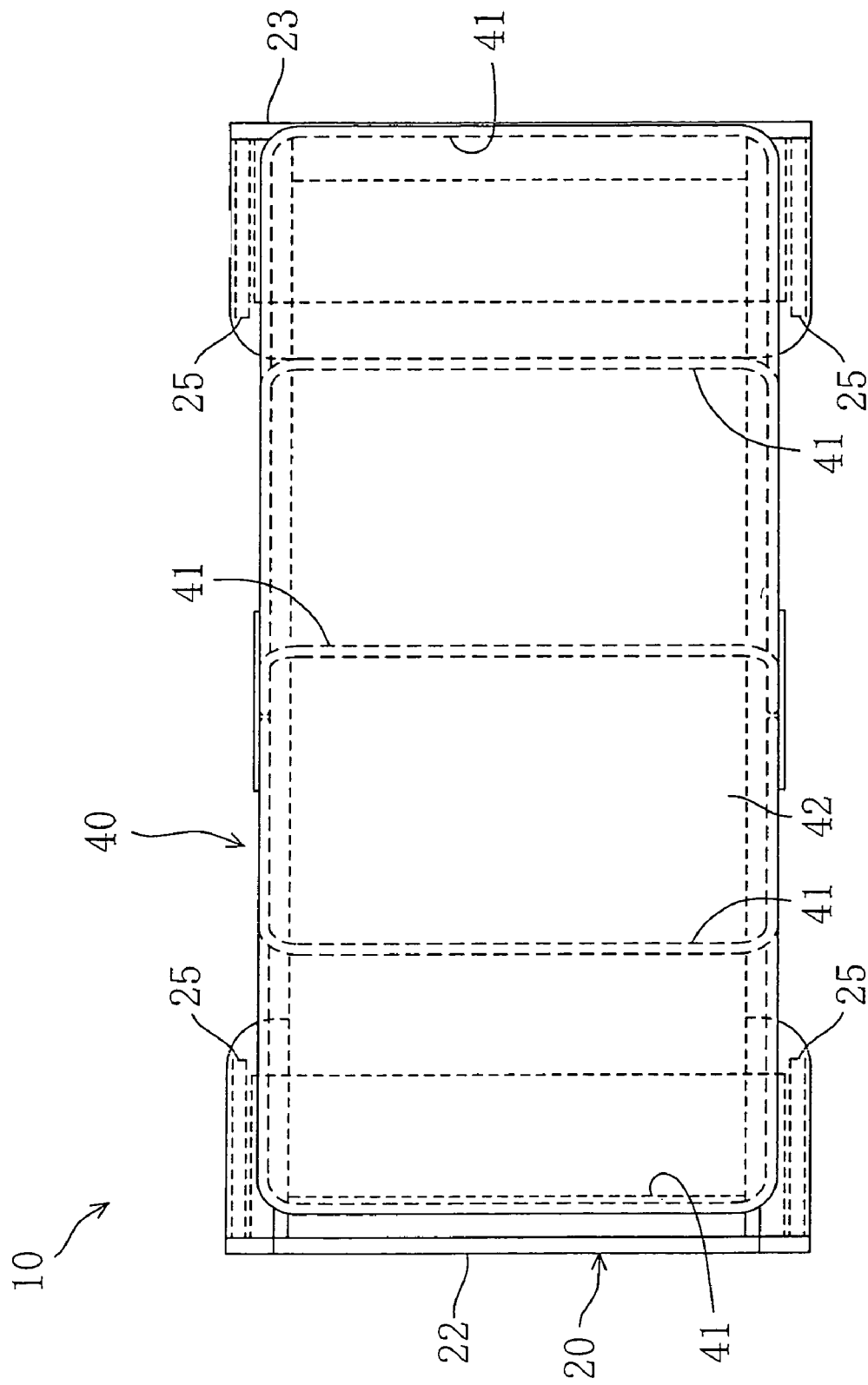

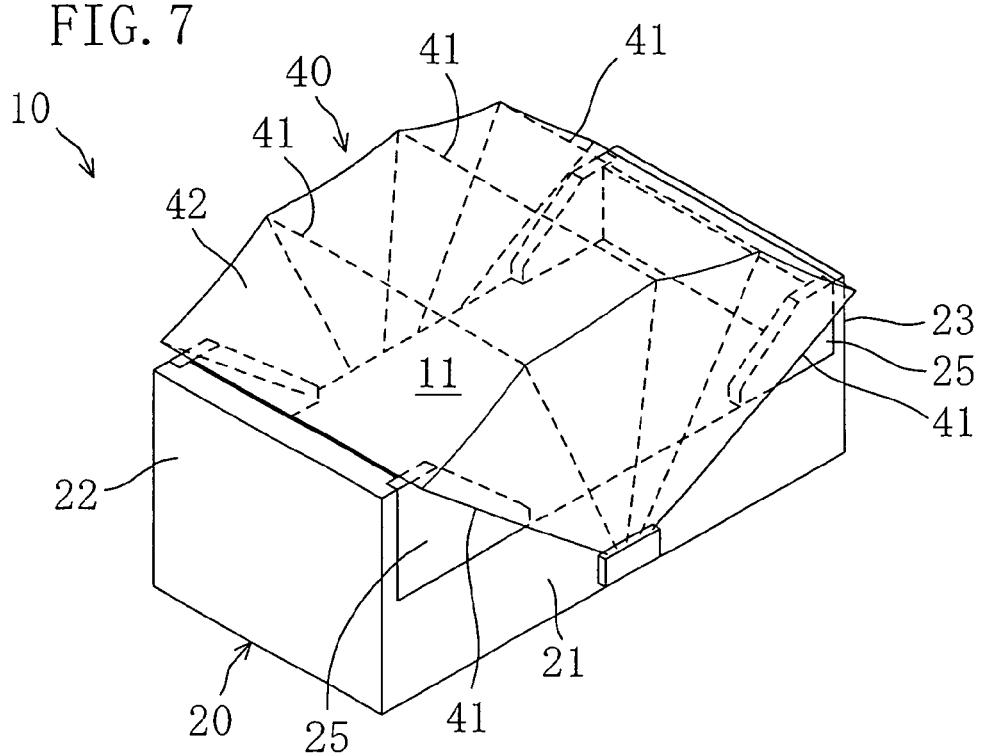
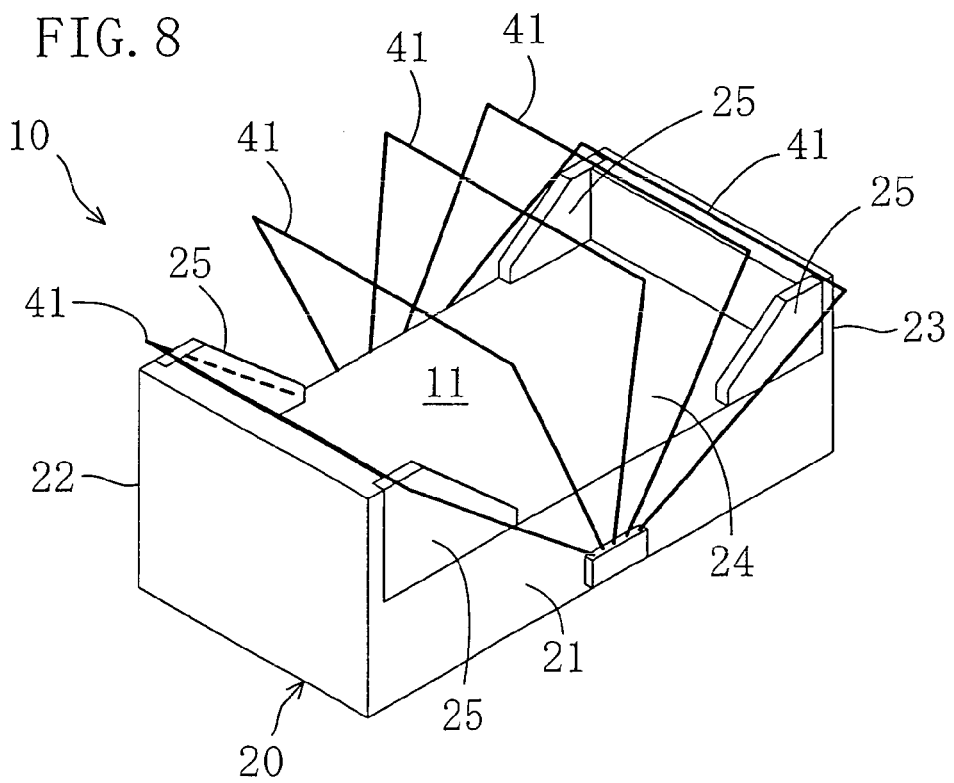

SLEEPING CAPSULE

TECHNICAL FIELD

The present invention relates generally to a capsule used for sleeping and more particularly concerns measures for the air conditioning of a sleeping compartment of such a sleeping capsule.

BACKGROUND ART

Some of previously known sleeping capsules are of the type in which an air outlet opening and an air inlet opening are so formed as to open to a sleeping compartment of a capsule main body, such as the one disclosed in Japanese Utility Model Kokai Publication No. (1992)100545. In such a conventional sleeping capsule, an evaporator is disposed midway along an air passageway by which the inlet opening and the outlet opening are connected together, and air cooled by the evaporator is supplied to the sleeping compartment.

Problems To Be Solved

In a sleeping capsule of the conventional type, indoor air drawn in through a single inlet opening formed at the feet of a sleeping person is cooled as described above. Thereafter, the indoor air thus conditioned is supplied to a sleeping compartment through a single outlet opening formed at the feet of the sleeping person. And, the sleeping capsule provides such air conditioning that a set temperature pre-selected by the sleeping person is maintained uniformly throughout the sleeping compartment.

The above-mentioned sleeping capsule, however, suffers from a problem that it is not suitable for providing thermo-physiologic comfort to the human body. In other words, examination of the optimal temperature of the human body by individual regions shows that the head is lowest in human body optimal temperature and the optimal temperature gradually increases from the head toward the feet. Stated another way, a so-called "keeping one's head cool and feet warm" temperature distribution is suitable for providing thermo-physiologic comfort to the human body.

Commonly-used sleeping capsules offer air conditioning control merely capable of keeping the entire sleeping compartment at a set temperature and therefore lack to give a comfort feeling to a sleeping person.

Bearing in mind the above-described problem, the present invention was made. Accordingly, an object of the present invention is to control a sleeping compartment of a capsule main body so that the sleeping compartment is placed in an air-conditioned state suitable for providing thermo-physiologic comfort to a sleeping person.

DISCLOSURE OF INVENTION

Summary of Invention

The present invention is designed to cause a local short circuit of conditioned air for the head and the feet of a sleeping person.

Problem Solving Means

More specifically, as shown in FIG. 2, a first invention comprises: a capsule main body (20); a head-side inflow/outflow unit (60) and a foot-side inflow/outflow unit (70), wherein the units (60) and (70) have a respective outlet opening (61, 71) for supplying conditioned air to a sleeping compartment (11) within the capsule main body (20) and a respective inlet opening (62, 72), associated with the outlet opening (61, 71), for drawing in internal air of the sleeping compartment (11), and wherein the units (60) and (70) are arranged in association with at least the head and feet of a sleeping person; and an air-conditioning control means (12) for controlling the air-conditioning capacity of conditioned air supplied through each of the outlet openings (61, 71) so that the temperature of conditioned air supplied through the outlet opening (61) of the head-side inflow/outflow unit (60) falls below the temperature of conditioned air supplied through the outlet opening (71) of the foot-side inflow/outflow unit (70). And, the head-side inflow/outflow unit (60) and the foot-side inflow/outflow unit (70) are so configured as to produce flow of an air current causing a short-circuit between the outlet opening (61, 71) and the inlet opening (62, 72).

In addition, a second invention according to the first invention is configured such that the inlet opening (62, 72) of the head-side inflow/outflow unit (60) or the foot-side inflow/outflow unit (70) is located below or above the outlet opening (61, 71).

Furthermore, a third invention according to either the first invention or the second invention is configured such that the outlet opening (61, 71) is provided with a wind direction changing plate (6e) for adjusting the direction in which air-conditioned air is supplied.

In addition, a fourth invention according to the first invention is configured such that the head-side inflow/outflow unit (60) or the foot-side inflow/outflow unit (70) is provided with a cowl body (65, 75) for forming an air-current space which covers the sleeping person's head or feet.

Furthermore, a fifth invention according to the first invention is configured such that the cowl body (65, 75) is provided with a wind direction changing plate (6r, 7r) for adjusting the flow of air-conditioned air.

To sum up, in the present invention, air-conditioned air supplied to the sleeping compartment (11) through the outlet opening (61) is drawn into the inlet opening (62), thereby causing a local short circuit. In other words, since most of the conditioned air from the outlet opening (61) is drawn directly into the inlet opening (62), this forms a short circuit region between the outlet opening (61) and the inlet opening (62), thereby providing air conditioning for the head of a sleeping person.

On the other hand, in the foot-side inflow/outflow unit (70), conditioned air supplied to the sleeping compartment (11) through the outlet opening (71) is drawn into the inlet opening (72), thereby causing a local short circuit. In other words, since most of the conditioned air from the outlet opening (71) is drawn directly into the inlet opening (72), this forms a short circuit region between the outlet opening (71) and the inlet opening (72), thereby providing air conditioning for the sleeping person's feet.

Especially in the second invention, the arrangement that the inlet opening (62) is located below the outlet opening (61) in the head-side inflow/outflow unit (60) ensures that a short circuit region is formed without fail because the conditioned air of the head-side inflow/outflow unit (60), since it is a current of cool air, is definitely drawn into the lower-situated inlet opening (62). On the other hand, the arrangement that the inlet opening (72) is located above the outlet opening (71) in the foot-side inflow/outflow unit (70) ensures that a short circuit region is formed without fail because the conditioned air of the foot-side inflow/outflow unit (70), since it is a current of warm, is definitely drawn into the upper-situated inlet opening (72).

In accordance with the third and fifth inventions, the flow of air-conditioned air is controlled by means of the wind direction changing plate (6e, 6r, 7r), thereby preventing a draft from flowing towards the sleeping person.

Effects of Invention

Accordingly, in accordance with the present invention, it is arranged such that the temperature of conditioned air supplied from the outlet opening (61) and the temperature of conditioned air supplied from the outlet opening (71) are controlled individually, which arrangement makes it possible to form the sleeping compartment (11) capable of providing thermo-physiologic comfort to the human body.

To sum up, it is possible to keep the sleeping person in a so-called "head cool and feet warm" temperature distribution condition based on the optimal temperature of the human body by individual body regions (in other words, the head is lowest in optimal temperature and the optimal temperature gradually increases from the head towards the feet). As the result of this, it is possible to improve the level of comfort of the sleeping person.

Furthermore, short circuit regions are formed between the outlet and inlet openings (61, 62) of the head-side inflow/outflow unit (60) and between the outlet and inlet openings (71, 72) of the foot-side inflow/outflow unit (70), thereby ensuring formation of a "head cool and feet warm" temperature distribution.

In addition, in accordance with the second invention, the arrangement that the inlet opening (62) is located below the outlet opening (61) in the head-side inflow/outflow unit (60) ensures that a short circuit region is definitely formed. More specifically, the conditioned air of the head-side inflow/outflow unit (60), since it is a current of cold wind, is definitely drawn into the lower-situated inlet opening (62).

Furthermore, the arrangement that the inlet opening (72) is located above the outlet opening (71) in the foot-side inflow/outflow unit (70) ensures that a short circuit region is definitely formed. More specifically, the conditioned air of the foot-side inflow/outflow unit (70), since it is a current of warm wind, is definitely drawn into the upper-situated inlet opening (72).

Additionally, in accordance with the third invention, since it is arranged such that the wind direction changing plate (6e) is provided in the outlet opening (61, 71), this arrangement definitely prevents a draft from flowing towards the sleeping person.

Furthermore, in accordance with the fourth invention, the cowl bodies (65, 75) for creating an air-current space which covers the sleeping person's head and an air-current space which covers the sleeping person's feet respectively are provided. As a result of such arrangement, short circuit regions are formed definitely, thereby making it possible to form a "head cool and feet warm" temperature distribution.

In addition, in accordance with the fifth invention, the cowl bodies (65, 75) are provided with the wind direction changing plates (6r, 7r) respectively, thereby making it possible to prevent a draft from flowing towards the sleeping person and to provide a cooling feeling by a current of air to the sleeping person.

BRIEF DESCRIPTION OF DRAWINGS

FIG. 5 is a side view showing a sleeping capsule of the first embodiment of the present invention;

FIG. 6 is a top plan view showing the sleeping capsule of the first embodiment of the present invention;

FIG. 7 is a perspective illustration showing the sleeping capsule of the first embodiment of the present invention;

FIG. 8 is a perspective view showing the sleeping capsule of the first embodiment of the present invention with the omission of a hood cloth thereof;

BEST MODE FOR CARRYING OUT INVENTION

Embodiment 1

Figure 1:
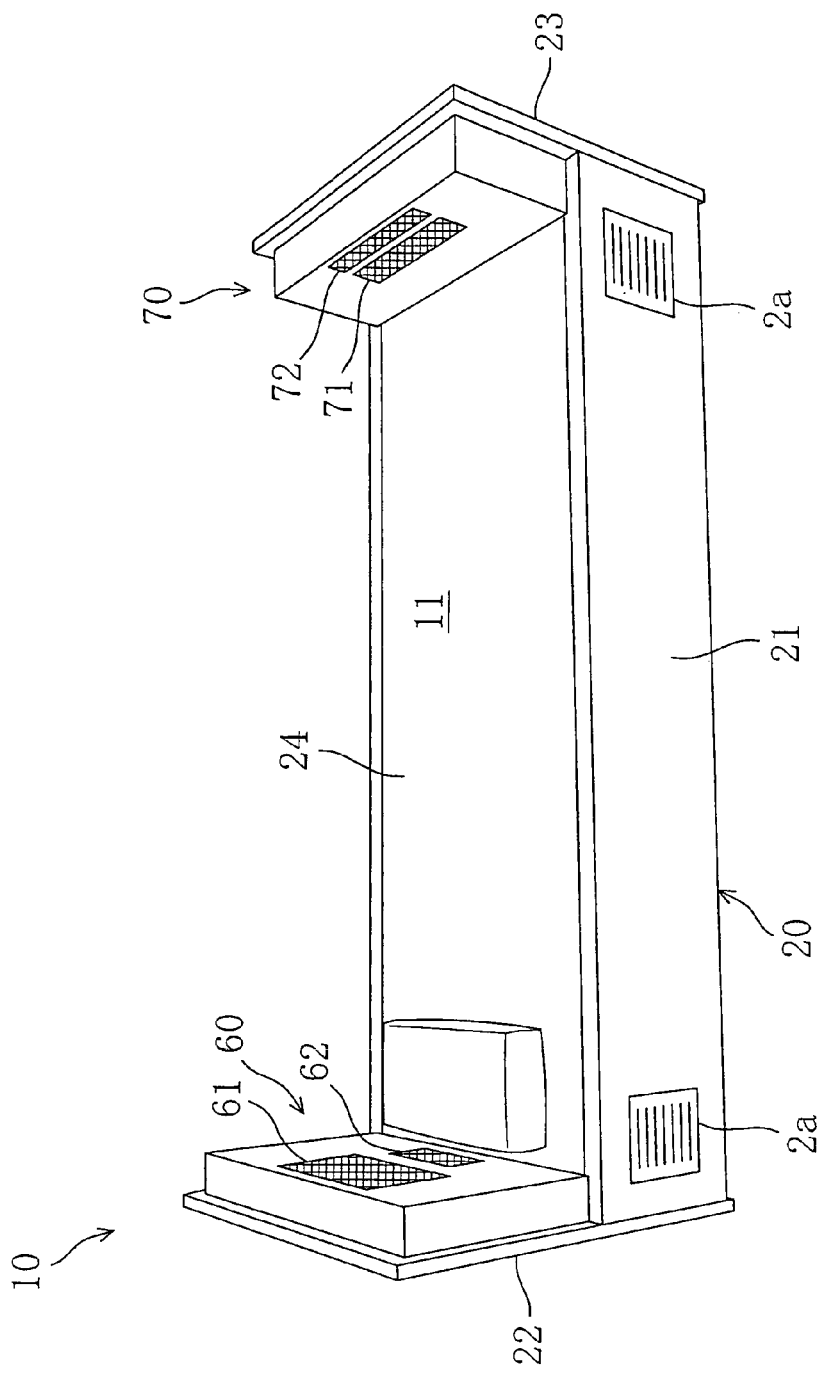
FIG. 1 is a perspective illustration showing a capsule main body according to a first embodiment of the present invention.
Figure 2:
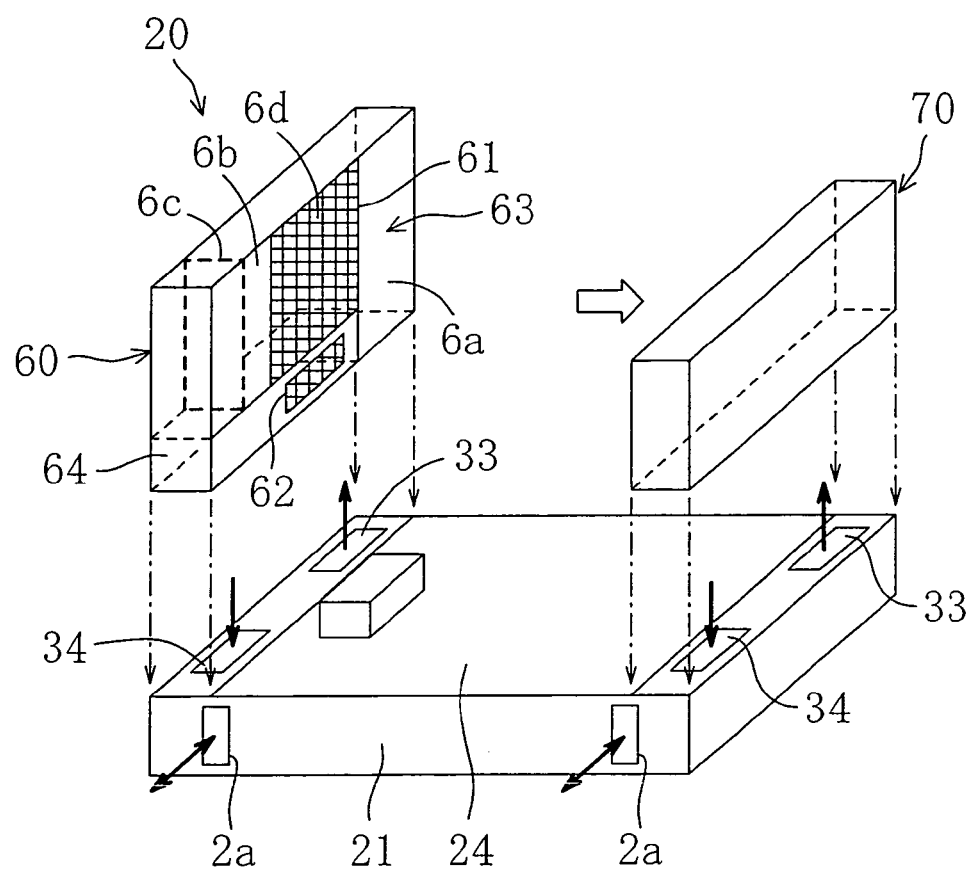
FIG. 2 is an exploded perspective illustration showing the capsule main body of the first embodiment of the present invention.
Figure 3:
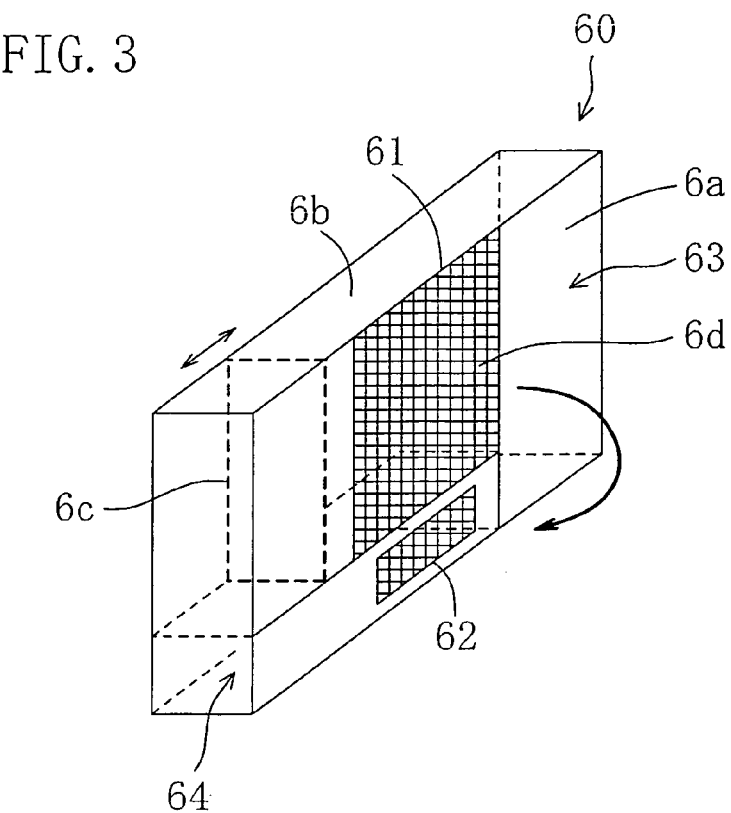
FIG. 3 is a perspective illustration showing a head-side inflow/outflow unit of the first embodiment of the present invention.
Figure 4:
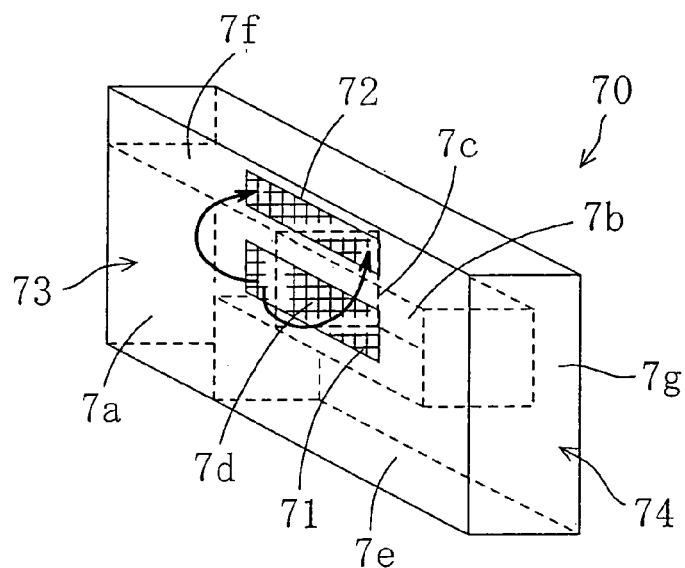
FIG. 4 is a perspective illustration showing a foot-side inflow/outflow unit of the first embodiment of the present invention.

Hereinafter, a first embodiment of the present invention will be described in detail with reference to the drawings.

As shown in FIGS. 1-11, a sleeping capsule (10) of the first embodiment is intended for use by a user who is going to take a nap or the like. The sleeping capsule (10) constitutes a relatively small, enclosed space for a user to sleep in.

The sleeping capsule (10) is configured such that that the sleeping capsule (10) includes a capsule main body (20) which is provided with two air conditioning systems, i.e., a head-side air conditioning system (3F) and a foot-side air conditioning system (3R).

The capsule main body (20) is made up of a floor platform (21), a head-side plate (22) arranged at the front of the floor platform (21) (on the side of the head of a sleeping person), a foot-side plate (23) arranged at the rear of the floor platform (21) (on the side of the feet of the sleeping person), and a covering member (40) for covering of both sides of the floor platform (21) and for providing cover above the floor platform (21). And the inside of the capsule main body (20) is formed into a sleeping compartment (11) which is a sleeping space, and the top of the floor platform (21) is formed into a sleeping bed (24) which is a sleeping area for the sleeping person to sleep in. To sum up, the covering member (40), the head-side plate (22), and the foot-side plate (23) together constitute a compartment member for the sleeping compartment (11).

As shown in FIGS. 5-8, the covering member (40) is shaped like a folding top (hood) and is provided with five support ribs (41) and a hood cloth (42). The five support ribs (41) each shaped like a gate and the lower ends of each of the support ribs (41) are attached to central parts of the floor platform (21) on both the sides thereof. The hood cloth (42) is attached to the five support ribs (41) so that the hood cloth (42) covers the five support ribs (41). And, of the five support ribs (41), the rearmost support rib (41) is fixedly attached to the floor platform (21) and to the foot-side plate (23) while the other four support ribs (41) are so constructed as to be able to rotate back-and-forth relative to the floor platform (21). Therefore, when the four rotatable support ribs (41) are rotated back-and-forth relative to the floor platform (21), the capsule main body (20) is opened and closed. Triangular auxiliary side plates (25) for closing gaps defined between the floor platform (21) and the covering member (40) are provided in both side parts at the front and the rear of the floor platform (21).

Figure 9:
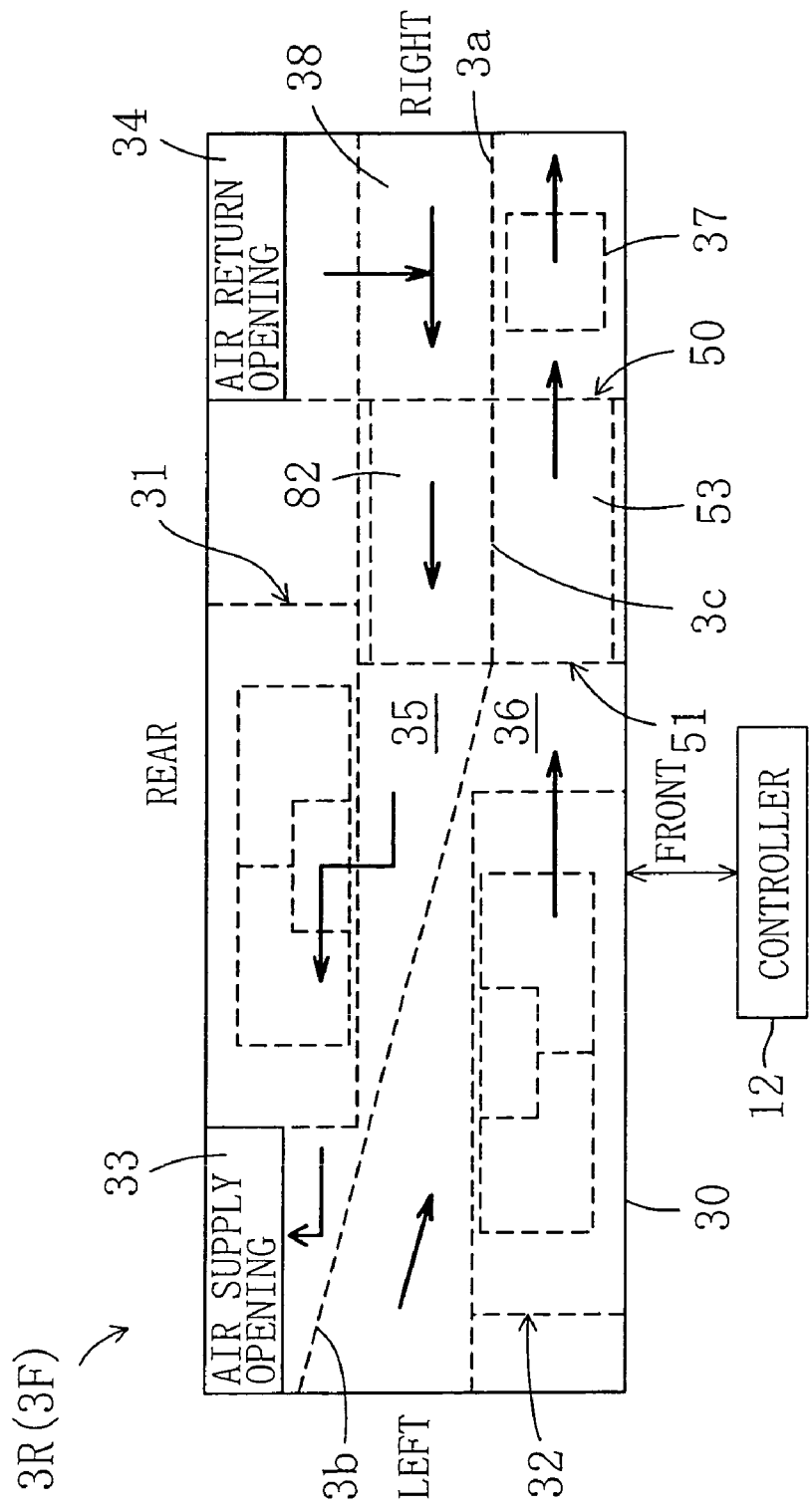
FIG. 9 is a top plan view showing an air conditioning system of the first embodiment of the present invention.
Figure 10:
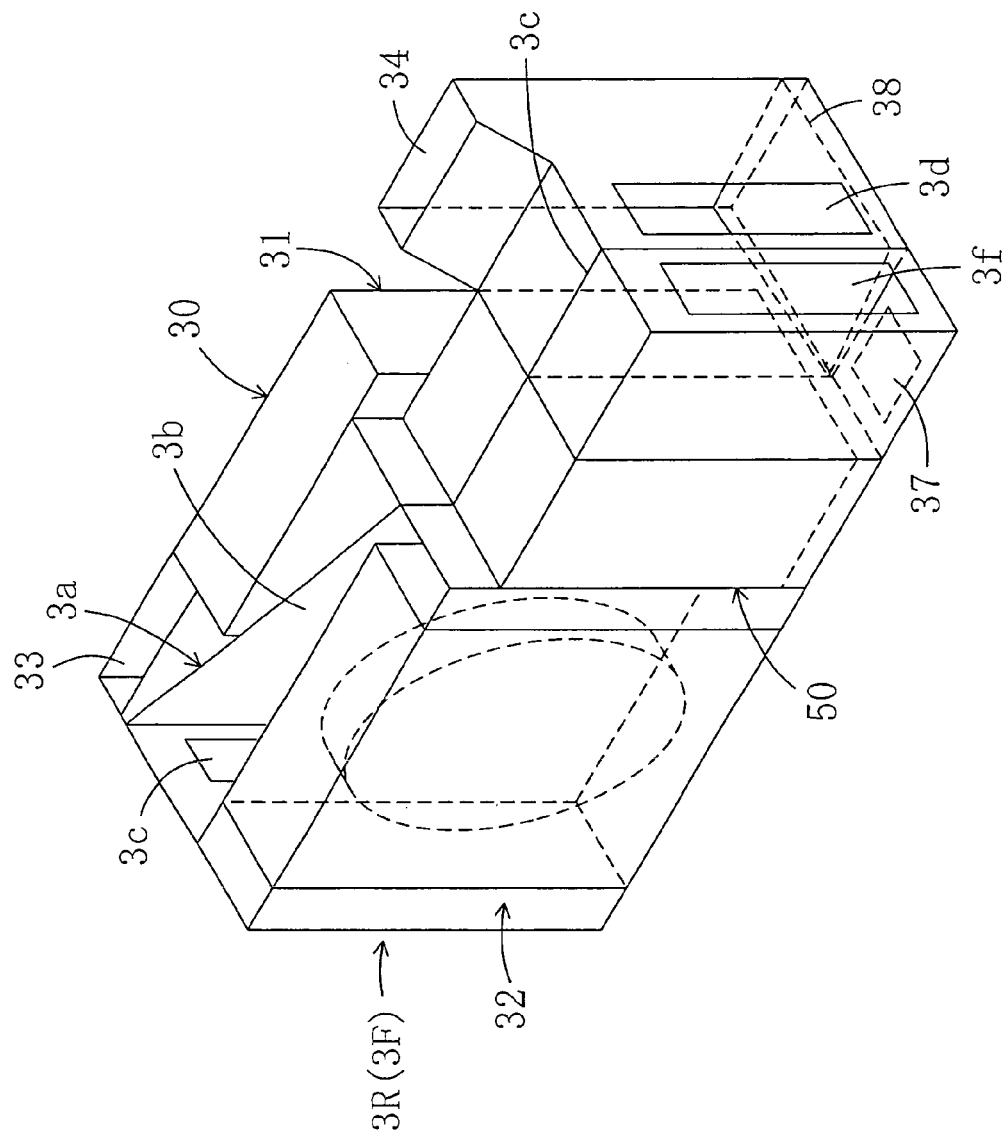
FIG. 10 is a perspective illustration, when viewed from the front, showing the air conditioning system of the first embodiment of the present invention.
Figure 11:
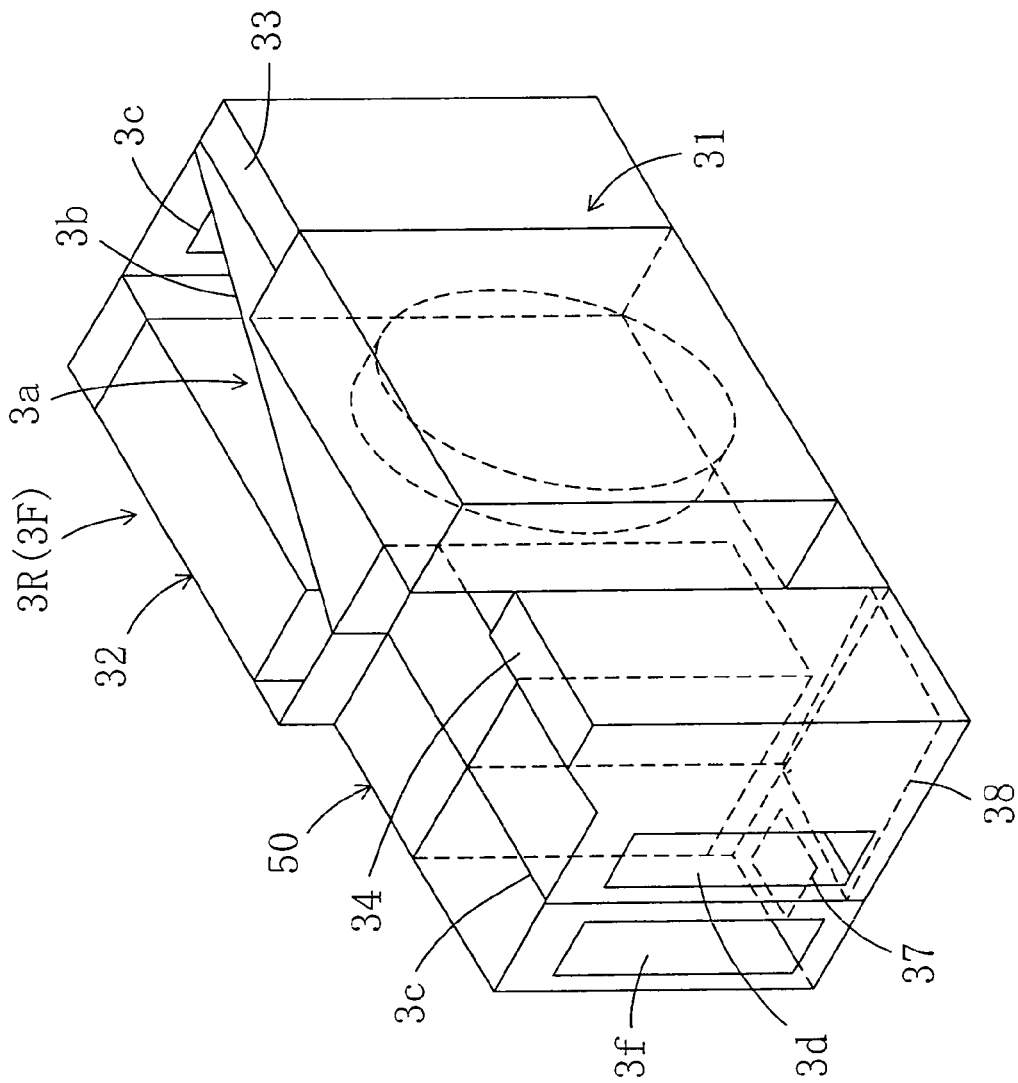
FIG. 11 is a perspective illustration, when viewed from the rear, showing the air conditioning system of the first embodiment of the present invention.

As shown in FIGS. 9-11, the head-side air conditioning system (3F) and the foot-side air conditioning system (3R) are each formed into a single unit comprising a single case (30) housing an air conditioning fan (31), a heat discharge fan (32), and a heat exchanging member (50). The head-side air conditioning system (3F) and the foot-side air conditioning system (3R) are disposed within the floor platform (21). And, each of the head-side air conditioning system (3F) and the foot-side air conditioning system (3R) is provided, at both side parts of the front and rear ends of the bed (24), with an air supply opening (33) and an air return opening (34). Since the head-side air conditioning system (3F) and the foot-side air conditioning system (3R) have substantially the same construction, only the foot-side air conditioning system (3R) will be described below. In the present invention, the side of the bed (24) is referred to as the front side.

The case (30) is shaped like a rectangle which is wider than it is long and is so formed as to extend from one side of the bed (24) to the other, and a partitioning plate (3*a*) is disposed in the inside of the case (30). The partitioning plate (3*a*) is so formed as to extend laterally from one side surface of the case (30) to the other. The partitioning plate (3*a*) is comprised of an inclined part (3*b*) which slopes towards both side surfaces of the case (30) on the front and rear sides and which extends from a left-hand side surface of the case (30) to substantially the center of the case (30), and a parallel part (3*c*) which is in parallel with both the side surfaces of the case (30) on the front and rear sides and is continuous with the inclined part (3*b*) and which extends to a right-hand side surface of the case (30).

Divisionally formed at the rear of the partitioning plate (3*a*) in the inside of the case (30) is an air conditioning passageway (35). A heat discharge passageway (36) is divisionally formed at the front of the partitioning plate (3*a*) in the inside of the case (30). And, the air supply opening (33) and the air return opening (34) are provided at both side parts in the rear of an upper surface of the case (30), being in communication with the air conditioning passageway (35).

In addition, the heat discharge fan (32) is disposed at the front of the inclined part (3*b*) of the partitioning plate (3*a*) in the heat discharge passageway (36). The air conditioning fan (31) is disposed at the rear of the inclined part (3*b*) of the partitioning plate (3*a*) in the air conditioning passageway (35). The air conditioning fan (31) and the heat discharge fan (32) are centrifugal fans, wherein a fan inlet opening is formed face to face with the inclined part (3*b*) of the partitioning plate (3*a*) and a fan outlet opening is formed in a part of the outer circumferential surface.

The heat exchanging member (50) is provided with a thermoelectric element (51) which is a so-called Peltier element. In the thermoelectric element (51), its two thermal surfaces are a heating surface and a cooling surface. Each thermal surface is provided with a large number of fins, i.e., a first fin group (52) and a second fin group (53). The thermoelectric element (51) is disposed such that it penetrates through the parallel part (3*c*) of the partitioning plate (3*a*) at substantially the center of the case (30) in a front-to-rear direction. And, the first fin group (52) is located in the air conditioning passageway (35), while the second fin group (53) is located in the heat discharge passageway (36).

An air conditioning outside air intake opening (3*d*) and a heat discharge opening (3*f*), which are in communication with an air opening (2*a*) formed at a side surface of the floor platform (21), are formed at a right-hand side surface of the case (30), while a heat discharge outside air intake opening (3*e*), which is in communication with an air opening formed at another side surface of the floor platform (21), is formed at a left-hand side surface of the case (30).

The air conditioning outside air intake opening (3*d*) opens at a side surface of the case (30) situated on the suction side of the air conditioning passageway (35) and on the side of the air return opening (34). Accordingly, inflow air from the air return opening (34) merges with outside air and the merged stream flows through the first fin group (52) of the thermoelectric element (51).

The heat discharge outside air intake opening (3*e*) opens at a side surface of the case (30) situated on the suction side of the heat discharge passageway (36) and on the side of the air supply opening (33). The heat discharge opening (3*f*) opens at a side surface of the case (30) situated on the supply side of the heat discharge passageway (36) and on the side of the air return opening (34). And, outside air from the heat discharge outside air intake opening (3*e*) flows through the second fin group (53) of the thermoelectric element (51), and is discharged outside through the heat discharge opening (3*f*).

Furthermore, an evaporation heater (37) is disposed at a bottom area of the case (30) in the heat discharge passageway (36). The evaporation heater (37) is provided to evaporate the dripping drain from the thermoelectric element (51). The evaporation heater (37) is disposed downstream of the second fin group (53) of the thermoelectric element (51). In addition, a drain receiver (38) is disposed at a bottom area of the case (30) in the air conditioning passageway (35). The drain receiver (38) guides the drain to the evaporation heater (37). The thermoelectric element (51) is oriented such that it slightly slopes towards the evaporation heater (37) and the drain receiver (38). As a result of such arrangement, the drain flows to the evaporator heater (37) and to the drain receiver (38).

A head-side inflow/outflow unit (60) is connected to the air supply opening (33) and the air return opening (34) of the head-side air conditioning system (3F), while a foot-side inflow/outflow unit (70) is connected to the air supply opening (33) and the air return opening (34) of the foot-side air conditioning system (3R).

The head-side inflow/outflow unit (60) has, at its head side on the front side of the bed (24), an outlet opening (61) and an inlet opening (62) and provides air conditioning mainly for the head of the sleeping person. And, the head-side inflow/outflow unit (60) is configured such that it produces flow of an air current causing a short circuit between the outlet opening (61) and the inlet opening (62). More specifically, the head-side inflow/outflow unit (60) is so configured as to form a short circuit region in front of the outlet and inlet openings (61) and (62).

The foot-side inflow/outflow unit (70) has, at its foot side on the rear side of the bed (24), an outlet opening (71) and an inlet opening (72) and provides air conditioning mainly for the feet of the sleeping person. And, the foot-side inflow/outflow unit (70) is configured such that it produces flow of an air current causing a short circuit between the outlet opening (71) and the inlet opening (72). More specifically, the foot-side inflow/outflow unit (70) is so configured as to form a short circuit region in front of the outlet and inlet openings (71) and (72).

The head-side inflow/outflow unit (60) is attached to the head-side plate (22) and is provided with a supply passageway (63) and a suction passageway (64). The supply passageway (63) includes a longitudinal passageway (6a) and a horizontal passageway (6b). The longitudinal passageway (6a) is formed in a side part of the head-side inflow/outflow unit (60), with its lower and upper ends in communication with the air supply opening (33) and with the horizontal passageway (6b), respectively. The horizontal passageway (6b) is formed at an upper part of the head-side inflow/outflow unit (60). And, the outlet opening (61) is formed such that the horizontal passageway (6b) opens at the front surface of the head-side inflow/outflow unit (60) situated face to face with the bed (24).

The horizontal passageway (6b) is provided with a partitioning plate (6c) serving as an adjusting means for adjusting the velocity of wind. The partitioning plate (6c) is formed laterally slidably along the horizontal passageway (6b) and is so configured as to control the velocity of conditioned air supplied through the outlet opening (61). The outlet opening (61) is provided with a distributing mesh (6d) for providing a uniform distribution of wind supply velocity and for making the air pressure of the supply passageway (63) positive.

The suction passageway (64) is located below the horizontal passageway (6b) and is in communication with the air return opening (34), and the inlet opening (62) is formed in the suction passageway (64). And, the inlet opening (62) opens at the front surface of the head-side inflow/outflow unit (60) situated face to face with the bed (24).

In the head-side inflow/outflow unit (60), the outlet opening (61) is located in the vicinity of the inlet opening (62), and the inlet opening (62) is located directly underneath the outlet opening (61). Furthermore, the inlet opening (62) is formed so as to have an opening area greater than that of the outlet opening (61) for the reduction in supply flow rate, thereby preventing a draft from flowing to the head of the sleeping person. The opening area of the inlet opening (62) is not necessarily made greater than that of the outlet opening (61). To sum up, the inlet opening (62) may have any opening area as long as it achieves a supply velocity capable of preventing a draft from flowing to the head of the sleeping person.

The foot-side inflow/outflow unit (70) is attached to the foot-side plate (23) and is provided with a supply passageway (73) and a suction passageway (74). The supply passageway (73) includes a longitudinal passageway (7a) and a horizontal passageway (7b). The longitudinal passageway (7a) is formed in a side part of the foot-side inflow/outflow unit (70), with its lower and upper ends in communication with the air supply opening (33) and with the horizontal passageway (7b), respectively. The horizontal passageway (7b) is formed centrally in the foot-side inflow/outflow unit (70). And, the outlet opening (71) is formed such that the horizontal passageway (7b) opens at the front surface of the foot-side inflow/outflow (70) situated face to face with the bed (24).

The horizontal passageway (7b) is provided with a partitioning plate (7c) serving as an adjusting means for adjusting the velocity of wind. The partitioning plate (7c) is formed laterally slidably along the horizontal passageway (7b) and is so configured as to control the velocity of conditioned air supplied through the outlet opening (71). The outlet opening (71) is provided with a distributing mesh (7d) for providing a uniform distribution of wind supply velocity and for making the air pressure of the supply passageway (73) positive.

The suction passageway (74) is provided with two horizontal passageways (7e, 7f) one of which is located above the horizontal passageway (7b) of the supply passageway (73) and the other of which is located below the horizontal passageway (7b) of the supply passageway (73). The suction passageway (74) is further provided with a longitudinal passageway (7g) which connects together the two horizontal passageways (7e, 7f). The lower-situated horizontal passageway (7e) is in communication with the air return opening (34), and the inlet opening (72) is formed in the upper-situated horizontal passageway (7f). And, the inlet opening (72) opens at the front surface of the foot-side inflow/outflow unit (70) situated face to face with the bed (24).

In the foot-side inflow/outflow unit (70), the outlet opening (71) is located in the vicinity of the inlet opening (72), and the inlet opening (72) is located directly above the outlet opening (71). Furthermore, the inlet opening (72) is formed so as to have an opening area greater than that of the outlet opening (71) for the reduction in supply flow rate, thereby preventing a draft from flowing to the feet of the sleeping person. The opening area of the inlet opening (72) is not necessarily made greater than that of the outlet opening (71). To sum up, the inlet opening (72) may have any opening area as long as it achieves a supply velocity capable of preventing a draft from flowing to the feet of the sleeping person.

The sleeping capsule (10) is provided with a controller (12) which is an air conditioning control means. The controller (12) controls the heat exchanging member (50) in order that the temperature of conditioned air supplied from the outlet opening (61) of the head-side inflow/outflow unit (60) can become a set temperature (ST). More specifically, the controller (12) controls the thermoelectric element (15) of the head-side air supply passageway (3a) which is continuous with the head-side inflow/outflow unit (60), and the temperature of air passing through the head-side air supply passageway (3a) is adjusted to the set temperature ST.

In addition, the controller (12) controls the heat exchanging member (50) so that the temperature of conditioned air supplied from the outlet opening (71) of the foot-side inflow/outflow unit (70) becomes higher than the set temperature ST by 4.0° C. (i.e., ST+4.0° C.). Stated another way, the controller (12) controls the thermoelectric element (51) of the foot-side air supply passageway (3a) which is continuous with the foot-side inflow/outflow unit (70) so that the temperature of air passing through the foot-side air supply passageway (3a) is adjusted to a value which is higher than the set temperature ST by 4.0° C.

By virtue of control by the controller (12), a "head cool and feet warm" temperature distribution is formed, thereby achieving a state suitable for human body thermal physiologic comfort.

Operation

In the next place, air conditioning operation of the above-mentioned sleeping capsule (10) will be described.

A user who is going to take for example a short nap rotates the covering member (40) towards the foot side of the sleeping capsule (10), climbs into the sleeping compartment (11), rotates the covering member (40) towards the head side, and sleeps on the sleeping bed (24). And, the user sets a set temperature (ST) by an operation box. Data indicative of the set temperature ST is fed to the controller (12).

When the air conditioning fan (31) and the heat discharge fan (32) are activated in each of the head- and foot-side air conditioning systems (3F) and (3R), air in the sleeping compartment (11) is drawn into the air conditioning passageway (35) through the air return opening (34) while simultaneously outside air is introduced into the air conditioning passageway (35) through the air conditioning outside air intake opening (3d). The air in the air conditioning passageway (35) passes through the first fin group (52) of the heat exchanging member (50), and is heated or cooled so that conditioned air is generated. In other words, in the thermoelectric element (51) there are formed a heating surface and a cooling surface, and the first fin group (52) is heated while the second fin group (53) is cooled during the heating mode of operation. On the other hand, during the cooling mode of operation, the first fin group (52) is cooled while the second fin group (53) is heated.

Of the conditioned air, a stream of conditioned air passes through the air supply opening (33), flows through the head-side inflow/outflow unit (60), and is supplied, through the outlet opening (61), into the sleeping compartment (11), while another stream of conditioned air passes through the air supply opening (33), flows through the foot-side inflow/outflow unit (70), and is supplied, through the outlet opening (71), into the sleeping compartment (11). To sum up, conditioned air which is supplied through the outlet opening (61) of the head-side inflow/outflow unit (60) is delivered towards the head of the sleeping person and is drawn into the lower-situated inlet opening (62). On the other hand, conditioned air which is supplied through the outlet opening (71) of the foot-side inflow/outflow unit (70) is delivered towards the feet of the sleeping person and is drawn into the upper-situated inlet opening (72).

The temperature of conditioned air which is supplied from the foot-side inflow/outflow unit (70) is adjusted by the thermoelectric element (51) such that the conditioned air temperature is higher than the set temperature ST by 4.0° C. On the other hand, the temperature of conditioned air which is supplied from the head-side inflow/outflow unit (60) is adjusted by the thermoelectric element (51) such that the conditioned air temperature is equal to the set temperature ST. As the result of this, the sleeping person sleeps in a "head cool and feet warm" temperature distribution condition.

The conditioned air supplied from the head-side inflow/outflow unit (60) is drawn into the inlet opening (62) of the head-side inflow/outflow unit (60), and flows through the air conditioning passageway (35) via the suction passageway (64), while on the other hand the conditioned air supplied from the foot-side inflow/outflow unit (70) is drawn into the inlet opening (72) of the foot-side inflow/outflow unit (70), and flows through the air conditioning passageway (35) via the suction passageway (74). Thereafter, the air returns to the air conditioning fan (31) by way of the air conditioning passageway (35) and the aforesaid operations are carried out repeatedly.

Meanwhile, outside air is introduced, through the heat discharge outside air intake opening (3e), into the heat discharge passageway (36). The air thus introduced into the heat discharge passageway (36) passes through the heat discharge fan (32). Then, the air is heated by, for example, the second fin group (53) of the thermoelectric element (51) and is discharged to outside the capsule main body (20) through the heat discharge opening (3f).

Furthermore, drain from the thermoelectric element (51), e.g., drain dripped from the first fin group (52) during the cooling mode of operation, is received in the drain receiver (38), flows through the evaporation heater (37), evaporates, and is discharged to the outside together with the air in the heat discharge passageway (36).

In the head-side inflow/outflow unit (60), conditioned air passes through the air supply opening (33), flows through the longitudinal and horizontal passageways (6a) and (6b) of the supply passageway (63), and is supplied, through the outlet opening (61), to the sleeping compartment (11). The arrangement that the inlet opening (62) is located directly underneath the outlet opening (61) causes a local short circuit. As the result of this, most of the conditioned air is drawn into the inlet opening (62) and flows to the air return opening (34) from the suction passageway (64). Accordingly, a short circuit region is formed in front of the outlet and inlet openings (61) and (62), thereby providing air conditioning for the head of the sleeping person.

In the foot-side inflow/outflow unit (70), conditioned air passes through the air supply opening (33), flows through the longitudinal and horizontal passageways (7a) and (7b) of the supply passageway (73), and is supplied, through the outlet opening (71), to the sleeping compartment (11). The arrangement that the inlet opening (72) is located directly above the outlet opening (71) causes a local short circuit. As the result of this, most of the conditioned air is drawn into the inlet opening (72) and flows to the air return opening (34) from the horizontal passageways (7e) and (7f) and the longitudinal passageway (7g) of the suction passageway (74). Accordingly, a short circuit region is formed in front of the outlet and inlet openings (71) and (72), thereby providing air conditioning for the feet of the sleeping person.

Working-Effects of First Embodiment

As has been described above, in accordance with the present embodiment, it is arranged such that the temperature of conditioned air which is supplied from the outlet opening (61) and the temperature of conditioned air which is supplied from the outlet opening (71) are controlled individually. As a result of such arrangement, it becomes possible to form the sleeping compartment (11) capable of providing thermal physiologic comfort to the human body.

To sum up, it is possible to keep the sleeping person in a so-called "head cool and feet warm" temperature distribution condition based on the optimal temperature of the human body by individual body regions (in other words, the head is lowest in optimal temperature and the optimal temperature gradually increases from the head towards the feet). As the result of this, it is possible to improve the level of comfort of the sleeping person.

Furthermore, short circuit regions are formed in front of the outlet and inlet openings (61, 62) of the head-side inflow/outflow unit (60) and in front of the outlet and inlet openings (71, 72) of the foot-side inflow/outflow unit (70), thereby ensuring formation of a "head cool and feet warm" temperature distribution.

In addition, in the head-side inflow/outflow unit (60) it is arranged such that the inlet opening (62) is located directly underneath the outlet opening (61), which arrangement makes it possible to ensure formation of a short circuit region. Especially, since conditioned air from the head-side inflow/outflow unit (60) is a stream of cool air, this ensures that the conditioned air is definitely drawn into the lower-situated inlet opening (62).

Furthermore, in the foot-side inflow/outflow unit (70) it is arranged such that the inlet opening (72) is located above the outlet opening (71), which arrangement makes it possible to ensure formation of a short circuit region. Especially, since conditioned air from the foot-side inflow/outflow unit (70) is a stream of warm air, this ensures that the conditioned air is definitely drawn into the upper-situated inlet opening (72).

Additionally, the provision of the distributing meshes (6d) and (7d) in the outlet openings (61) and (71) of the head- and foot-side inflow/outflow units (60) and (70) further ensures formation of a short circuit region.

Furthermore, the provision of the partitioning plates (6c) and (7c) in the supply passageways (63) and (73) of the head- and foot-side inflow/outflow units (60) and (70) makes it possible to control the velocity of supply wind. As the result of this, it is ensured that a short circuit region is formed without fail.

Embodiment 2

Hereinafter, a second embodiment of the present invention will be described in detail with reference to the drawings.

Figure 12:
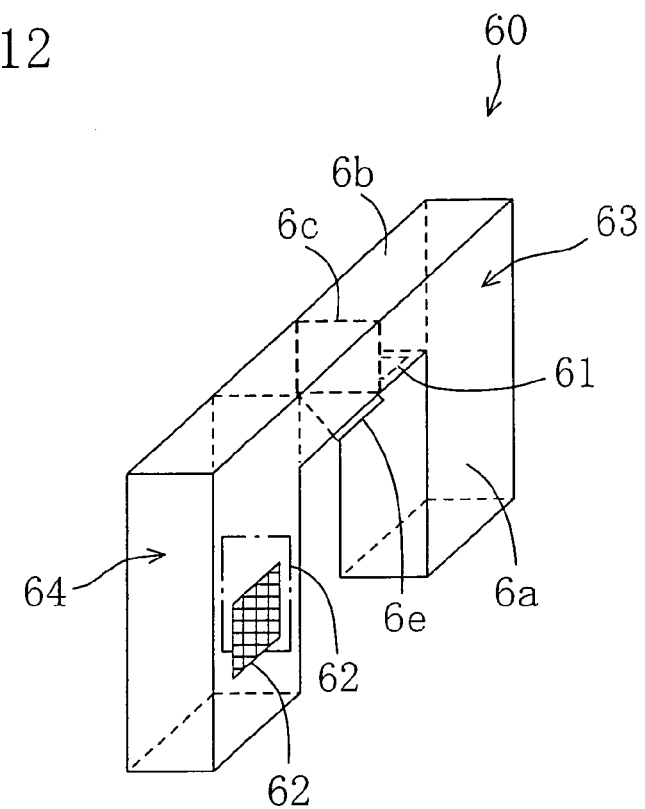
FIG. 12 is a perspective illustration showing a head-side inflow/outflow unit according to a second embodiment of the present invention.
Figure 13:
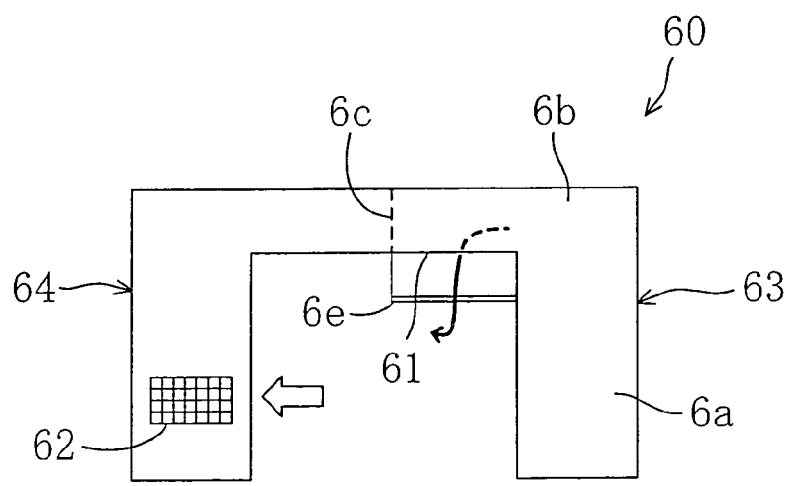
FIG. 13 is a front view showing the head-side inflow/outflow unit of the second embodiment of the present invention.

Referring to FIGS. 12 and 13, there is shown a head-side inflow/outflow unit (60) according to a second embodiment of the present invention. Unlike the head-side inflow/outflow unit (60) of the first embodiment which is shaped like a box which is thin in the front-to-rear direction, the head-side inflow/outflow unit (60) of the second embodiment is shaped like a gate which is thin in the front-to-rear direction.

More specifically, the head-side inflow/outflow unit (60) of the second embodiment includes a supply passageway (63) which is provided with a longitudinal passageway (6a) and a horizontal passageway (6b). The longitudinal passageway (6a) is formed in a side part of the head-side inflow/outflow unit (60). The longitudinal passageway (6a) has a lower end and an upper end, wherein the former is in communication with the air supply opening (33) while the latter is in communication with the horizontal passageway (6b). The horizontal passageway (6b) is formed in an upper part of the head-side inflow/outflow unit (60) and an outlet opening (61) is formed at an underside surface of the horizontal passageway (6b). In addition, in the underside surface of the horizontal passageway (6b), a wind direction changing plate (6e), for changing the direction in which air-conditioned air is supplied, is provided at a front side of the outlet opening (61).

On the other hand, the suction passageway (64) is located on the opposite side to the longitudinal passageway (6a) of the supply passageway (63) and is formed in a longitudinal direction. And, the air supply passageway (3a) is in communication with the air return opening (34) and an inlet opening (62) is formed at an inner surface which is a front surface.

The horizontal passageway (6b) is provided with a partitioning plate (6c), as in the first embodiment. In addition, the inlet opening (62) is located under the outlet opening (61). Furthermore, the inlet opening (62) is formed so as to have a greater opening area than that of the outlet opening (61).

Additionally, as indicated by a dashed line of FIG. 12, the inlet opening (62) may be formed at an inner side surface.

In accordance with the present embodiment, in the head-side inflow/outflow unit (60), conditioned air passes through the air intake opening (33), flows through the longitudinal and horizontal passageways (6a) and (6b) of the supply passageway (63), and is supplied, through the outlet opening (61), into the sleeping compartment (11). Thereafter, the conditioned air is made to flow forwardly to the head of the sleeping person by the wind direction changing plate (6e), and is drawn into the suction passageway through the inlet opening (62).

As the result of this, it is ensured that a short circuit region is formed for the head of the sleeping person. In addition, the wind direction changing plate (6e) ensures that a draft flowing to the sleeping person is prevented and it is possible to provide, to the sleeping person, a cooling feeling generated by an air current. Other constructions and operation/working-effects are the same as the first embodiment.

Embodiment 3

Hereinafter, a third embodiment of the present invention will be described in detail with reference to the drawings.

Figure 14:
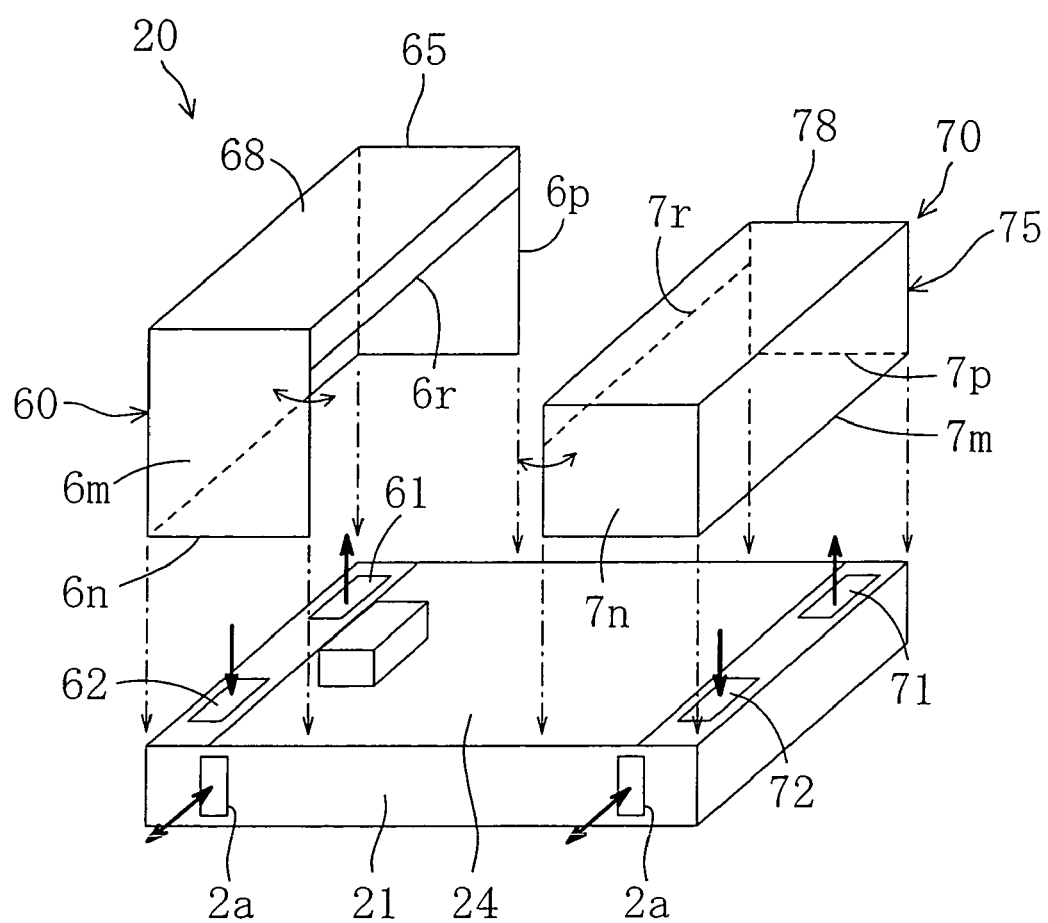
FIG. 14 is an exploded perspective illustration showing a capsule main body according to a third embodiment of the present invention.
Figure 15:
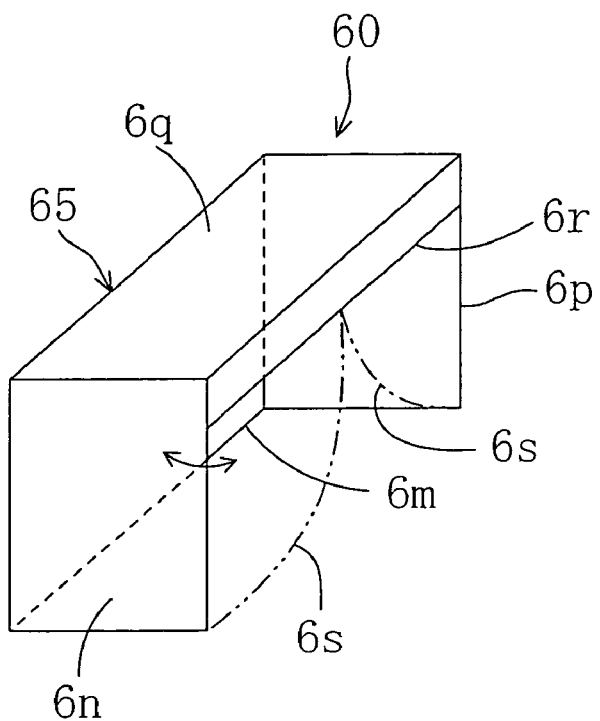
FIG. 15 is a perspective illustration showing a head-side inflow/outflow unit of the third embodiment of the present invention.
Figure 16:
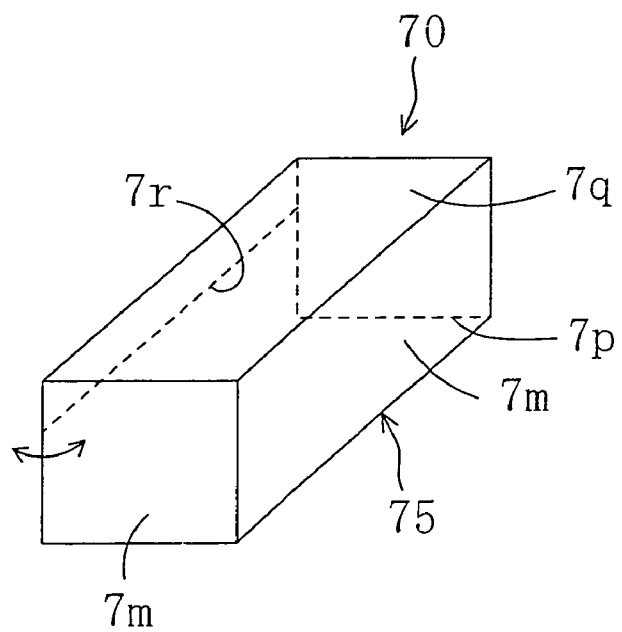
FIG. 16 is a perspective illustration showing a foot-side inflow/outflow unit of the third embodiment of the present invention.

Unlike the arrangement of the first embodiment that the head- and foot-side inflow/outflow units (60, 70) form respective short circuit regions in front of the outlet and inlet openings (61) and (62) and in front of the outlet and inlet openings (71) and (72), in the present embodiment short circuit regions are formed above the outlet and inlet opening (61, 62) and above the outlet and inlet openings (71) and (72), as shown in FIGS. 14-16.

The head-side inflow/outflow unit (60) and the foot-side inflow/outflow unit (70) are cowl-shaped so as to cover the head and the feet of a sleeping person.

More specifically, the head-side inflow/outflow unit (60) is provided with a cowl body (65) made up of a front plate (6m) which becomes the head-side plate (22) of the capsule main body (20), lateral side plates (6n, 6p), and a ceiling plate (6q), wherein the cowl body (65) is shaped like a box whose front surface facing the inside of the bed (24) is opened. And, the air supply opening (33) and the air return opening (34) in the first embodiment become the outlet opening (61) and the inlet opening (62) respectively, and the outlet opening (61) and the inlet opening (62) open to the interior of the cowl body (65). The interior of the cowl body (65) is formed into a short circuit region.

In addition, a wind direction changing plate (6r) for controlling the flow of air-conditioned air is provided at a front-surface upper end of the cowl body (65), extending laterally from one end of the cowl body (65) to the other. The wind direction changing plate (6r) rotates backward and forward on the upper side as a supporting point, thereby preventing a draft from flowing towards the head of the sleeping person and providing a cooling feeling by an air current.

On the other hand, the foot-side inflow/outflow unit (70) is provided with a cowl body (75) made up of a rear plate (7m) which becomes the foot-side plate (23) of the capsule main body (20), lateral side plates (7n, 7p), and a ceiling plate (7q), wherein the cowl body (75) is shaped like a box whose front surface facing the inside of the bed (24) is opened. And, the air supply opening (33) and the air return opening (34) of the first embodiment become the outlet opening (71) and the inlet opening (72) respectively, and the outlet opening (71) and the inlet opening (72) open to the interior of the cowl body (75). The interior of the cowl body (75) is formed into a short circuit region.

In addition, a wind direction changing plate (7r) for controlling the flow of air-conditioned air is provided at a front-surface upper end of the cowl body (75), extending laterally from one end of the cowl body (75) to the other. Furthermore, preferably the level of the ceiling plate (7q) is low because warm wind is supplied from the foot-side inflow/outflow unit (70), so that the ceiling plate (7q) is disposed at a lower level than the head-side inflow/outflow unit (60).

As indicated by a dashed line of FIG. 15, it may be arranged such that a front cover (6s) made of cloth or the like may be provided over the opening portion of the head-side inflow/outflow unit (60).

Accordingly, in the present embodiment, streams of conditioned air supplied upwardly from the outlet openings (61, 71) strike against the ceiling plates (6q, 7q) in the inside of the cowl bodies (65, 75), change direction downwardly, and are drawn into the inlet openings (62, 72), thereby ensuring formation of short circuit regions. And, since the head and feet of the sleeping person are within the cowl bodies (65) and (75), this makes it possible to form air flow spaces which cover the head and feet of the sleeping person, thereby ensuring formation of a "head cool and feet warm" temperature distribution.

In addition, the provision of the wind direction changing plates (6r, 7r) for the cowl bodies (65, 75) definitely prevents a draft from flowing to the sleeping person and provides a cooling feeling by an air current for the sleeping person. Other constructions and operation/working-effects are the same as the first embodiment.

Embodiment 4

Hereinafter, a fourth embodiment of the present invention will be described in detail with reference to the drawings.

Figure 17:
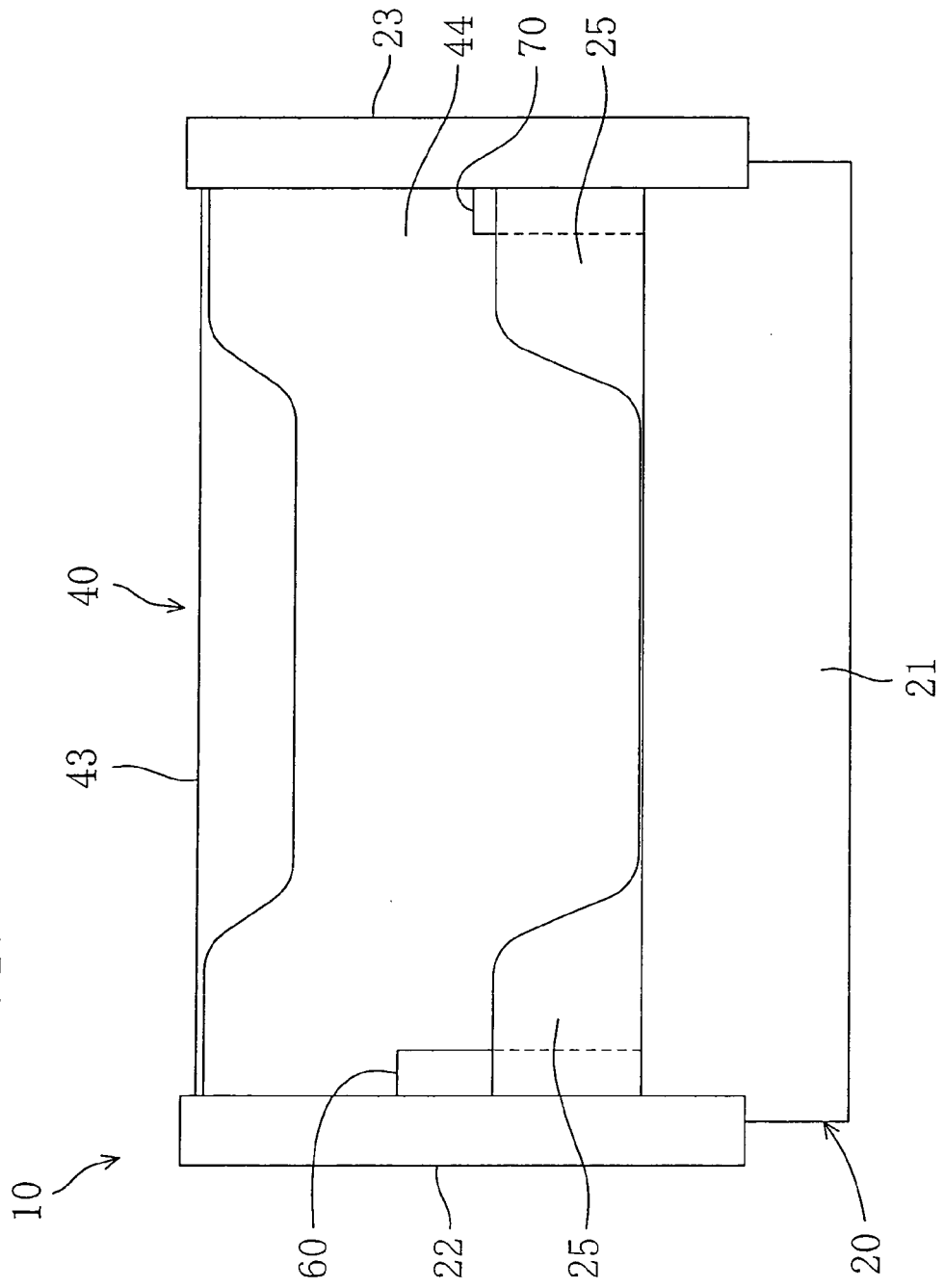
FIG. 17 is a side view showing a sleeping capsule according to a fourth embodiment of the present invention.
Figure 18:
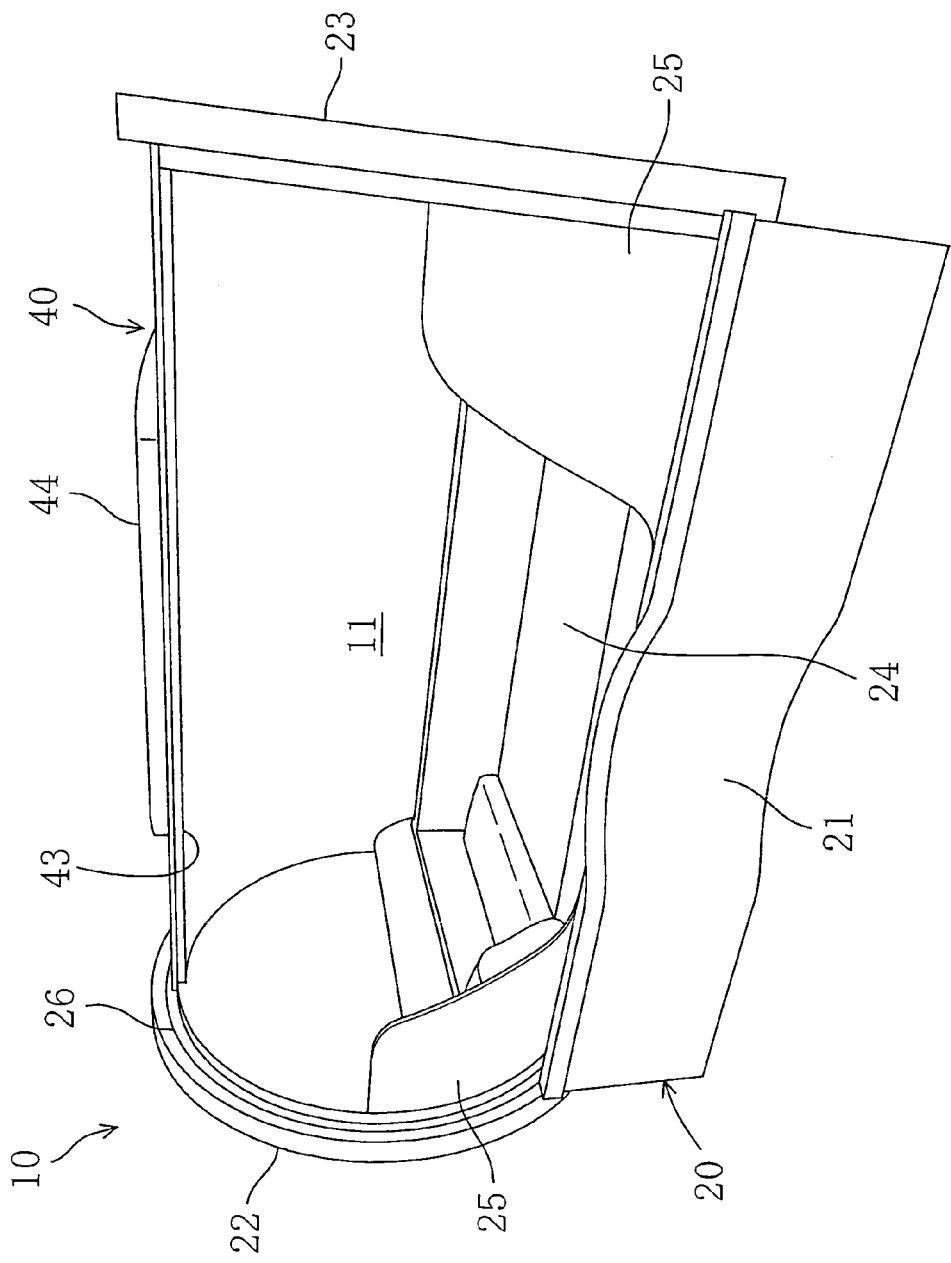
FIG. 18 is a perspective illustration showing the sleeping capsule of the fourth embodiment of the present invention when placed in the open position.
Figure 19:
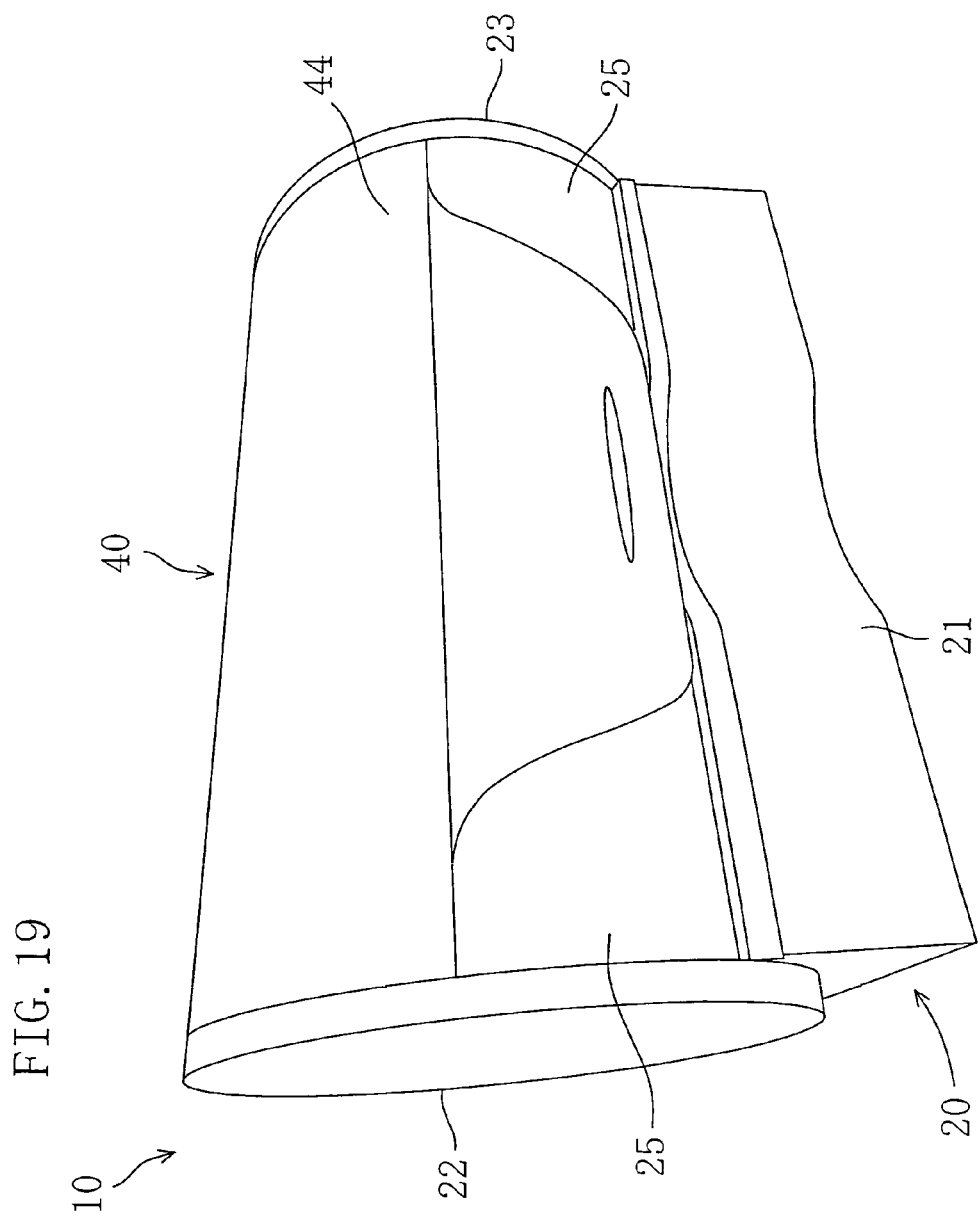
FIG. 19 is a perspective illustration showing the sleeping capsule of the fourth embodiment of the present invention when placed in the closed position.
Figure 20:
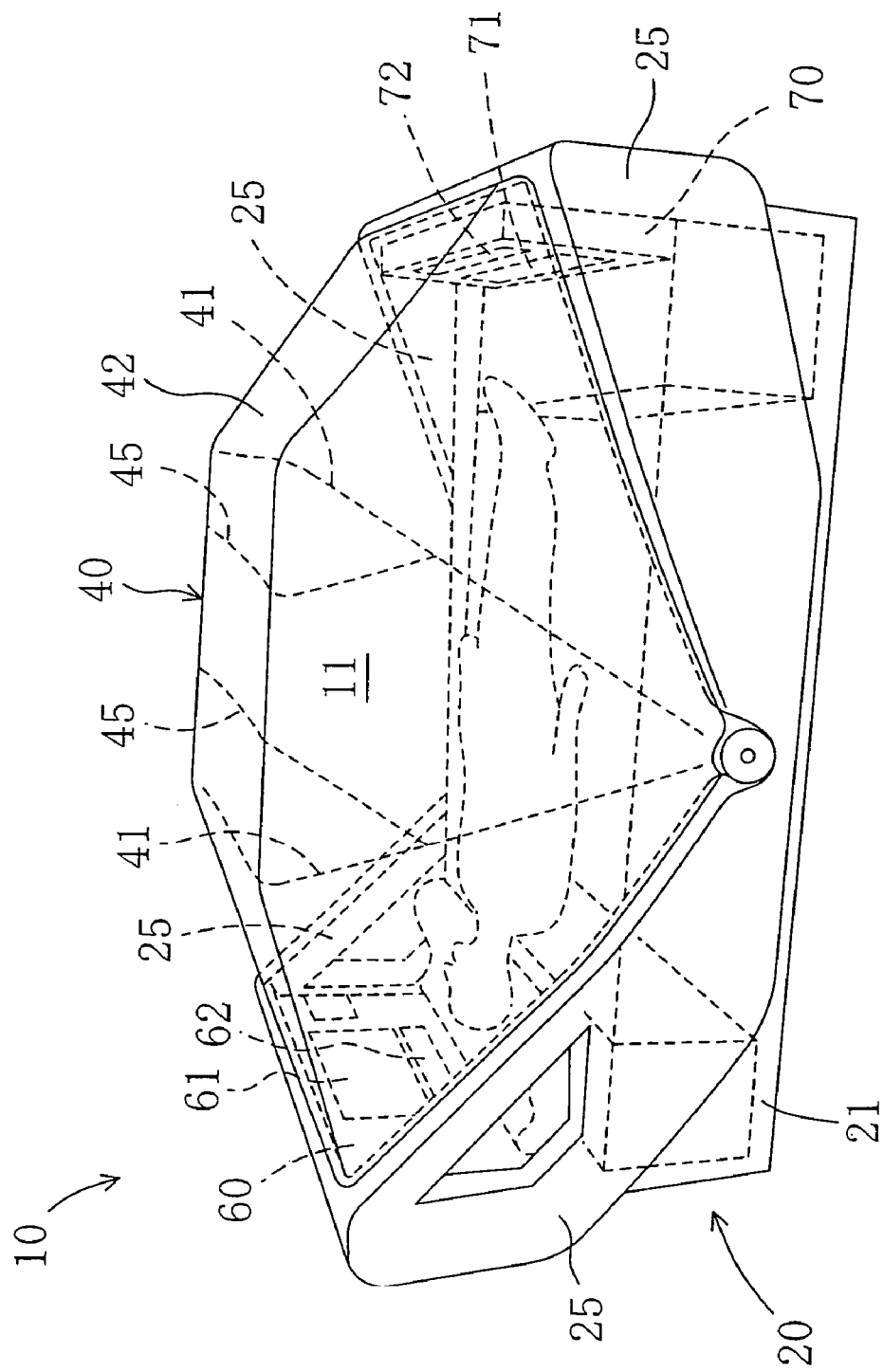
FIG. 20 is a perspective illustration showing a sleeping capsule according to a fifth embodiment of the present invention.
Figure 21:
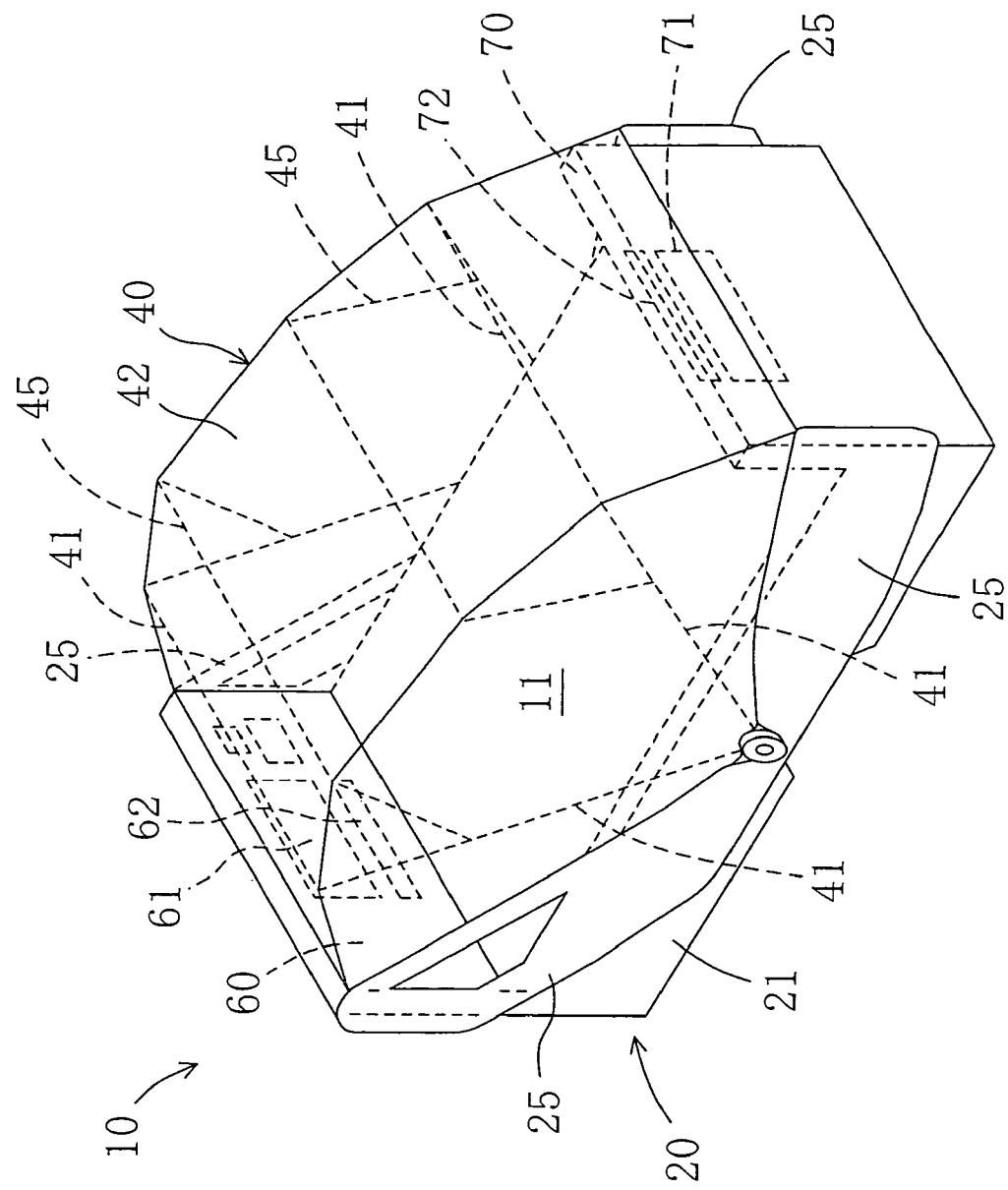
FIG. 21 is a perspective illustration showing the sleeping capsulate of the fifth embodiment of the present invention, when viewed from a different direction.

Unlike the arrangement of the first embodiment that the covering member (40) which is shaped like a hood is employed, the present embodiment employs a covering member (40) which is substantially cylinder-shaped, as shown in FIGS. 17-19.

More specifically, the head-side plate (22) and the foot-side plate (23) of the capsule main body (20) are disc-shaped. And, the covering member (40) is provided with a fixed cover (43) which covers an upper right half portion of the floor platform (21) and a movable cover (44) which covers an upper left half portion of the floor platform (21). The fixed cover (43) and the movable cover (44) are circular arc-shaped.

The movable cover (44) can be rotated along guide grooves (26) formed on the periphery of the head- and foot-side plates (22) and (23) so that the capsule main body (20) is opened and closed. Auxiliary side plates (25) are provided at side parts in the front and the rear of the floor platform (21). The auxiliary side plates (25) become continuous with the movable cover (44) when the movable cover (44) is placed in the closed position.

In the present embodiment, the user rotates the movable cover (44) to get into or out of the sleeping compartment (11). Other constructions and operation/working-effects are the same as the first embodiment.

Embodiment 5

Hereinafter, a fifth embodiment of the present invention will be described in detail with reference to the drawings.

Unlike the arrangement of the first embodiment that the covering member (40) is provided with the five support ribs (41), the present embodiment employs a covering member (40) which is provided with auxiliary ribs (45).

More specifically, the covering member (40) of the present embodiment is provided with four support ribs (41) and two auxiliary ribs (45). The four support ribs (41) are gate-shaped and their lower ends are fixed to central parts of both sides of the floor platform (21). In addition, the auxiliary ribs (45) are also gate-shaped and are attached to two centrally-located support ribs (41).

Of the four support ribs (41), the rearmost support rib (41) is fixed to the floor platform (21) and to the foot-side plate (23) while the three other support ribs (41) are constructed such that they are allowed to rotate back and forth relative to the floor platform (21).

When the aforesaid three support ribs (41) are rotated backward relative to the floor platform (21), the four support ribs (41) and the two auxiliary ribs (45) are folded to the rear of the capsule main body (20). Triangular auxiliary side plates (25) for closing gaps between the floor platform (21) and the covering member (40) are so formed as to smoothly become continuous with the central part of the floor platform (21). Other constructions and operation/working-effects are the same as the first embodiment.

Other Embodiments

In each of the foregoing embodiments, the head-side inflow/outflow unit (60) and the foot-side inflow/outflow unit (70) are provided. However, it may be arranged such that another inflow/outflow unit for air-conditioned air is provided midway between the head and the feet.

In addition, the heat exchanging member (50) is not limited to the thermoelectric element (51). For example, the heat exchanging member (50) may be implemented by an evaporator or condenser of the vapor compression type refrigeration cycle.

INDUSTRIAL APPLICABILITY

As has been described above, the present invention provides a sleeping capsule useful for the air conditioning of a sleeping compartment, particularly useful for the case of "head cool and feet warm" air conditioning.

What is claimed is:

1. A capsule used for sleeping comprising:
   a capsule main body,
   a head-side inflow/outflow unit and a foot-side inflow/outflow unit, wherein said units have a respective outlet opening for supplying conditioned air to a sleeping compartment within said capsule main body and a respective inlet opening, associated with said outlet opening, for drawing in internal air of said sleeping compartment, and wherein said units are arranged in association with at least the head and feet of a sleeping person,
   air-conditioning control means for controlling the air-conditioning capacity of conditioned air supplied through each of said outlet openings so that the temperature of conditioned air supplied through said outlet opening of said head-side inflow/outflow unit falls below the temperature of conditioned air supplied through said outlet opening of said foot-side inflow/outflow unit,
   wherein said head-side inflow/outflow unit is configured such that said inlet opening and said outlet opening are formed along a common vertical plane of said head-side inflow/outflow unit and is constructed to produce flow of an air current causing an air circulation path between said outlet opening and said inlet opening and wherein the inlet opening and the outlet opening are operated with the conditioned air flowing out from the outlet opening and the internal air and the conditioned air flowing in from the inlet opening.

2. The sleeping capsule of claim 1, wherein said inlet opening of said head-side inflow/outflow unit is located below or above said outlet opening.

3. The sleeping capsule of claim 1, wherein said outlet opening is provided with a wind direction changing plate for adjusting the direction in which air-conditioned air is supplied.

4. The sleeping capsule of claim 1, wherein said head-side inflow/outflow unit or said foot-side inflow/outflow unit is provided with a cowl body for forming an air-current space which covers said sleeping person's head or feet.

5. The sleeping capsule of claim 4, wherein said cowl body is provided with a wind direction changing plate for adjusting the flow of air-conditioned air.

6. The sleeping capsule of claim 1, wherein said foot-side inflow/outflow unit is so constructed as to produce flow of an air current causing an air circulation path between said outlet opening and said inlet opening.

7. The sleeping capsule of claim 1, wherein said inlet opening of said foot-side inflow/outflow unit is located below or above said outlet opening.

8. The sleeping capsule of claim 1, wherein said foot-side inflow/outflow unit is configured such that said inlet opening and said outlet opening are formed along a common vertical plane of said foot-side inflow/outflow unit and is constructed to produce flow of an air current causing an air circulation path between said outlet opening and said inlet opening and wherein the inlet opening and the outlet opening are operated with the conditioned air flowing out from the outlet opening and the internal air and the conditioned air flowing in from the inlet opening.

* * * * *